United States Patent [19]

Hoffman et al.

[11] 4,063,644

[45] Dec. 20, 1977

[54] PROCESS FOR NONDESTRUCTIVE INSPECTION

[75] Inventors: Kenneth G. Hoffman, Massapequa Park; Robert R. Maller, Plainview; Robert W. Messler, Jr., Farmingdale, all of N.Y.

[73] Assignee: Grumman Aerospace Corporation, Bethpage, N.Y.

[21] Appl. No.: 731,700

[22] Filed: Oct. 12, 1976

Related U.S. Application Data

[63] Continuation of Ser. No. 379,077, July 13, 1973, abandoned.

[51] Int. Cl.$^2$ .................. B07C 5/342; G01N 21/16
[52] U.S. Cl. ................................. 209/111.6; 204/1T; 356/32; 356/237
[58] Field of Search ............ 204/129.1, 129.2, 129.75, 204/35 R, 36, 1 T; 73/88 R; 209/111.6; 356/32, 237

[56] References Cited

U.S. PATENT DOCUMENTS

| | | | |
|---|---|---|---|
| 2,314,604 | 3/1943 | van der Horst | 204/35 R X |
| 2,430,750 | 11/1947 | Webersinn et al. | 204/36 |
| 2,947,674 | 8/1960 | Andrisek et al. | 204/35 R X |

*Primary Examiner*—G. L. Kaplan

[57] ABSTRACT

A process for the nondestructive inspection of chromium-plated or coated metal parts. The process uses an uncomplicated electrolytic technique to etch selectively the surface of the part to thereby develop indications of thermal damage which are readily detectable by a simple visual inspection without the requirement for any further processing of the part for inspection. The process is particularly suitable for the nondestructive detection of thermal damage in hard chromium plating on a high-strength steel base metal. Damage in the base metal of the part itself, particularly that resulting from abusive grinding or other machining operations on the plating, can also be detected in the chromium plating on the part because of the excellent correlation between chromium damage and base metal damage. In the process, after the part has undergone normal pre-etch preparation, it is immersed anodically in a conventional electrolytic solvent of the plating metal and is etched for a short period of time. Thermal damage to the plating and damage induced in the base metal through the chromium plate is indicated on the surface of the plating by color anomalies which delineate the areas of damage. No further processing is required for a reliable detection of thermal damage; however, means for enhancing the visual presentation are also set forth.

5 Claims, No Drawings

PROCESS FOR NONDESTRUCTIVE INSPECTION

This is a continuation of application Ser. No. 379,077, filed July 13, 1973, now abandoned.

BACKGROUND OF THE INVENTION

1. Field of the Invention

The present invention relates to a process for nondestructive testing of test pieces for thermal damage. More particularly, the invention relates to a nondestructive test process for detecting grinding-induced and related thermal damage to chromium-plated metal workpieces in which an electrochemical etching technique is used to cause indications of damaged areas to appear on the test piece surface as color anomalies.

2. Description of the Prior Art

The prior art shows a number of examples of nondestructive test methods such as magnetic particle, radiography, eddy current, ultrasonic, liquid crystal, and fluorescent penetrant; however, only the fluorescent penetrant and magnetic particle inspection processes lend themselves to relatively low cost per unit part on high rates of production. The value of these processes are degraded because they are limited to the detection of relatively gross flaws or discontinuities which have openings to the surface of the test parts.

It is also a requirement in the inspection of certain parts that the presence of structural or metallurgical damage to the base metal and chromium be revealed by the inspection method. Prior art methods, such as radiography, used for detecting subsurface defects and damage suffer from the drawbacks of being excessively tedious and of requiring cumbersome equipment, or they are expensive to use and are not readily adaptable to high-volume test scheduling. Radiography is limited also in that it only detects voids. In addition, because of limitations inherent in its resolving power, radiography is restricted in its ability to "see" defects which are small relative to the thickness of the test piece and the method is also restricted by considerations of part geometry.

It has been found, with respect to eddy current and ultrasonic testing, that the methods are substantially ineffective in chromium plate due to the extraneous indications produced by current density induced residual stress variations. The utility of these prior art eddy current and ultrasonic resting techniques is degraded also in that they are tedious and require interpretation of the test results.

A further limitation of the listed prior art methods is that they are all dependent on surface defects such as cracks and the like to produce indications of damage and they are largely ineffective with respect to the detection of structural alterations or thermally residual stress changes.

In the prior art, J. R. Alburger (U.S. Pat. No. 3,530,045) discloses a nondestructive testing method for electrically conductive metallic coated and plated parts for the detection of surface and subsurface defects on a high rate of production basis. In the Alburger method, the workpiece is immersed either anodically or cathodically in an electrolyte solution of an electrochemical system having an electrode of opposite polarity and an electric current is passed through the electrolyte and the workpiece and other electrode: the electrolyte solution is such that, either a coating is plated out of the solution onto the surface of the workpiece, the thickness of the coating being dependent upon the local current density, or, the $p^H$ of a $p^H$-sensitive liquid is altered locally near the surface due to current density variations resulting from surface or subsurface discontinuities to thus produce color changes. Surface or subsurface defects in the workpiece cause a variation in current density which results also in variations in the thickness of the coating applied on the workpiece. When the workpiece is removed from the electrolyte solution, the variations in coating thickness produce variations in the coating which are detectable visually to thereby also indicate surface or subsurface defects.

It will be seen therefore, that Alburger's process relies on current density effects on either a $p^H$-sensitive coating or on a deposited layer. Moreover, it will also be recognized that the process of Alburger is critically dependent on the composition of the electrolytic solution and its successful utilization is largely keyed to the presence of defects which act as physical discontinuities or breaks in the workpiece surface or subsurface. Also, unlike the subject process in which an etching or removal of surface material occurs, Alburger plates a coating of material on the workpiece surface, which coating provides the color variations that are used to indicate surface and subsurface defects.

SUMMARY OF THE INVENTION

The subject comprises a process for the nondestructive inspection of chromium-plated metal parts for surface and subsurface thermally induced damage. The process is particularly suitable for the inspection of chromium-plated, high-strength steel parts. In the normal electroplating of hard chromium, even in precision plating processes, it is normally not possible to prevent overplating which results in excessive deposits. This overplating presents a quality control problem, particularly in close-tolerance cylindrical parts. In order to finish such parts to obtain the tolerances required, the chromium-plated surface must be worked, usually by grinding, to achieve the necessary final diametrical dimensions and surface finish. During the process of metal removal by grinding, considerable heat is generated. Heat developed during grinding causes the chromium to expand locally and then rapidly contract due to the dissipation of the heat into the underlying mass of metal. As will be appreciated, as the rate of metal removal increases, the amount of frictionally generated heat increases. An excessive amount of metal removal due to too rapid an infeed rate, or too rapid a traverse speed has come to be known as "abusive" grinding. For the past few years it has been recognized that abusive grinding of hard-chromium plate on a high-strength steel base metal can result in thermally-induced damage to the chromium plate and, under certain conditions, to the base metal as well.

Damage to the hard chromium plate generally manifests itself as a coarse (but usually microscopic) "mud crack" or "chicken wire" pattern throughout the much finer inherent crack structure normally present in electrodeposited chromium. It is believed that this coarse crack pattern probably results primarily from thermal shock caused by rapid expansion due to high local grinding heat followed by a drastic contraction of the chromium because of a rapid flow of the generated heat into the substrate mass. Unlike the fine inherent crack pattern in electrodeposited chromium, these coarse grinding cracks (or "checks", as they are commonly termed) penetrate through the chromium plate to the base metal, permitting general corrosive attack or stress corrosion-cracking of the steel substrate.

In addition to the thermally induced damage usually manifesting itself as cracking and an alteration of residual stresses in the chromiumplate, abusive grinding can produce thermal damage such as overtempering and "burning" in the high-strength steel base metal. In hardened and tempered high-strength steels such as low alloy steels, heat-treated to 220 KSI and above ($R_c$ 46 and above) and Martensitic stainless steels heat-treated to 240 KSI and above ($R_c$ 49 and above), abusive grinding temperatures between 500°–1400° F can overtemper and soften the surface resulting in what is usually referred to as overtempered martensite. If the temperature exceeds 1400° F, a phenomenon commonly known as "burning" results in the formation of a hard, brittle layer of what is commonly called "untempered martensite". The presence of either a soft, overtempered condition or a hard, brittle untempered martensite condition normally produces residual tensile stresses in the base metal surface. In addition to residual tensile stresses, the damaged areas can also develop cracks; either of which condition, because of their stress concentrating effects, adversely affects the life and integrity of the component. Moreover, damage in the substrate in combination with a cracked chromium plating and normal service stresses can promote stress-corrosion cracking in the presence of a corrosive media.

It has been a practice in the prior art, where abusive grinding damage in a chromium plated part has been suspected, to remove all of the plating by an electrochemical process to thereby expose the metal substrate for inspection using suitable known test techniques, i.e., magnetic particle, nital etch, and the like. If the part was found to be undamaged, it was rechromed for re-use. Inasmuch as a grinding operation on the chromed part was then required to obtain the required size and finish, there was always the possibility that grinding damage could occur in a part that has obstensibly passed inspection such that a failure of the part could subsequently occur in service.

It will be appreciated that thermal damage can also occur in a sound part due to heat generated by friction under severe use in service (e.g., wear damage).

The subject invention meets the requirement for the nondestructive inspection of chromium-plated metal parts for detecting the aforementioned abusive grinding and friction-induced thermal damage. The invention comprises an electrochemical test technique using an etching process for obtaining a "color" indication delineating areas of surface and subsurface thermal damage in the part. In the technique, after it has undergone a suitable conventional pre-etch or plating cleaning procedure, the workpiece is immersed anodically in an electrolyte and a current is passed through the workpiece and the electrolyte. Following this procedure, the part can be inspected visually for areas of non-uniform surface appearance indicating surface and subsurface thermally induced damage.

It is an important object of the invention, therefore, to provide a nondestructive test process for the rapid detection of surface and subsurface damage in coated or plated test pieces, which process serving to produce anomalies in the surface appearance of the test piece to indicate thermal damage thereto such that defective parts can be detected by a simple visual inspection.

A further object of the invention is to provide an electrochemical test process in which thermal surface and subsurface damage in the test piece is indicated by color anomalies in the surface, which process uses only readily available conventional electrolytic solutions such that the requirement for specially formulated color-forming plating and coating solutions is thereby eliminated.

A still further object of the invention is to provide a nondestructive test process which is particularly effective in detecting surface and subsurface thermal damage in hard chromium plated high-strength steel parts.

These and other objects of the invention will in part be obvious and will in part become apparent in the light of the description which follows.

DESCRIPTION OF THE PREFERRED EMBODIMENTS

The workpiece to be inspected can be any chromium-plated metal part but, as stated previously, the method is particularly suited for the detection of thermal damage in hard chromium plated, high-strength steel parts. Therefore, in the description which follows of a preferred embodiment of the process of this invention, the test piece as set forth is a hard chromium plated, high-stressed steel component, but it will be appreciated that such emphasis in this description is not intended to imply that the invention is restricted solely thereto.

With reference now to preferred steps in the process of the invention, the test item or workpiece is prepared for test by first removing all component subassemblies, if any, such as bushings, pins, grease fittings, and the like. Finishes such as paint are removed using a solvent or paint remover appropriate to the finish; other finish systems should be masked using any suitable plastic film, tape, and the like. Foreign material such as metal pickup from galling with a mating component should be removed by etching or other suitable process. If the workpiece is to be racked, it should be racked such that good electrical contact is provided to thereby avoid point or loose contacts which cause arcing that can result in burning of the workpiece in that area. Clean the workpiece to obtain a clean, "water-break" free surface. The workpiece can be cleaned by immersing it for 1–5 minutes in any suitable alkaline cleaner and/or the workpiece can be wiped or scrubbed with a paste composed of powdered pumice or aluminum oxide and water. Either or both cleaning techniques can be used and repeated as required to obtain clean, water-break free surface. Follow the cleaning step with a rinse for a minimum of 30 seconds in water at ambient temperature. It will be appreciated that the aforementioned preparatory steps comprise essentially a conventional pre-etch procedure and can vary therefrom to any extent necessary to insure that the workpiece is properly prepared.

With the workpiece anodic, it is immersed in the electrolyte of an electrochemical system and an electric current is passed therethrough for between 30–120 seconds. The various parameters of the electrochemical system are maintained such that a chromium plating removal or de-plating of about 0.0001 inch/inch diameter/minute etch time is achieved. After the etching step, the workpiece is removed from the electrolyte and inspected for indications of damage.

In the electrochemical system used to etch the workpiece, the electrolyte can be composed of solutions having any of a suitable variety of compositions which have a solvent effect on the plating on the workpiece being inspected. In this process the electrochemical solution can be either acidic or alkaline; however, alkaline solutions are preferred for high-strength steels to avoid hydrogen contamination. With chromium plating, the composition most commonly used in the electrolyte is:

Potassium or sodium pyrophosphate (optimum concentration — 0.5 – 2 oz/gal), and
Potassium or sodium hydroxide (optimum concentration — 16 – 32 oz/gal).

Solution temperature can range from ambient to 150° F, ambient to 90° F is preferred, and the preferred distance between anode and cathode is 3 – 8 inches. Solution pH range should be 9 – 14 and the density of the solution 20°– 30° Baume. Etching voltage suitably is 12 v DC minimum with a current density of between 2 to 4 amps/in$^2$, depending upon the size of the workpiece. A high-viscosity polysulfonate surfactant may be used in the above solutions. Other solutions used successfully include: potassium or sodium carbonate and potassium or sodium hydroxide; chromic acid; hydrochloric acid; each of which may be used with a high viscosity polysulfonate surfactant. Other solutions which have produced effective results to date include materials marketed by M & T Chemicals, Inc., subsidiary of American Can Co., Rahway, N.J., under the labels of Unichrome Compound Nos. 80 and 80X.

The workpiece can be inspected immediately after the etching step, but it is preferred to first rinse it in water, preferably warm water to facilitate rinsing and/or drying, for a minimum of 30 seconds. To avoid removal of deposits that can serve to enhance indications of damage, the workpiece should not be rubbed nor washed after etching. If it is desired to dry the workpiece, forced air drying or a similar technique is preferred.

Detection of damage may be made easier if the workpice, whether wet or dry, is inspected under a directional light source which illuminates the workpiece surface at a low angle of incidence and perpendicular to the grinding direction. Inspection is preferably conducted using normal incandescent illumination; however, inspection has been successfully accomplished using other light sources and at other angles of incidence and directions. In the visual inspection of the workpiece, areas of the chromium surface that the etching step has caused to appear lighter or darker than the normal chromium background appearance indicates thermal damage in the chromium and possible damage to the steel substrate. A uniform chromium surface color or appearance after the etching step indicates that the workpiece has not undergone thermal damage in either the chromium or the steel substrate.

Although there may be some other mechanism which contributes to the success in the detection of surface and substrate thermal damage of the process of the invention, it is believed to be effective because of the effect of the abusive grinding heat on the residual stress patterns developed in the chromium plate. Areas in the chromium which have different residual stresses due to different degrees of thermal damage etch at different rates, and, consequently, the surface appearance of those areas differs from undamaged as-plated or properly ground chromium after etching. It will be appreciated that the anomalies in the surface appearance may be referred to as having a different color although in a large number of cases they probably should be understood to be hues or tones of the background color.

The overheating due to abusive grinding, in addition to damaging the chromium plate, can also produce thermal damage in the hardened and tempered high-strength steel base metal in a pattern which reflects the severity of the abusive grinding damage in the chromium plate. Thus, the damage which appears as a discolored area on the chromium has been shown to be representative, in severe cases of damage, in the steel base metal as well as in the chromium plate itself.

The relative severity of the grinding damage is reflected directly by the intensity of the etch indication even though the process removes only a substantially minute amount of the chromium plate. Also, because of the insignificant amount of the surface removed, which may be about 0.0001 inch in a normal size part, for example, the process of this invention can be considered to be almost completely nondestructive to either the chromium plating or to the metal substrate.

It has been found that the basic process as described without modification provides a reliable inspection method for thermally induced damage in plated parts. The etch indication can be photographed if a permanent record of the damage pattern in the workpiece is desired; however, if for some reason, a more pronounced color contrast is desired, the process can be followed by subsequent steps in which color intensifiers, dyes (fluorescent or regular), stains, indicators, and smut enhancers, and the like, are used to enhance the etch indication.

Although shown and described in what is believed to be the most practical and preferred embodiments, it is apparent that departures from the specific process and apparatus described will suggest themselves to those skilled in the art and may be made without departing from the spirit and scope of the invention. We, therefore, do not wish to restrict ourselves to the particular methods illustrated and described, but desire to avail ourselves of all modifications that may fall within the scope of the appended claims.

Having thus described our invention, what we claim is:

1. The process of non-destructive inspection for thermal damage in a chromium layer comprising the steps of:
   preparing a chromium plated article to be inspected to obtain a "water-break" free surface;
   deplating the chromium surface about 0.00005–0.0002 inch by having the article immersed in an electrolyte of an electrochemical system and passing electric current through said article for a period of time required to obtain the limited deplating;
   illuminating the chromium surface by a directional light source;
   pinpointing areas of the chromium surface having different coloration than the normal background appearance; and
   rejecting articles having different coloration due to thermal damage than the background.

2. The process of claim 1 wherein the deplating is in an electrolyte solution, alkaline in nature held to a temperature that ranges from ambient to 150° F and the distance from the article to cathode ranges from 3 to 8 inches with voltage being no less than 12 volts DC at a current density between 2 to 4 amps/in$^2$.

3. The process of claim 2 wherein the article is dried after the deplating and before illuminating the chromium surface without affecting surface qualities.

4. The process of claim 3 wherein the article is connected as the anode and the electrolyte is an acidic solution.

5. The process of claim 1 wherein the directional light source is by incandescent lighting at a low angle of incidence to the surface.

* * * * *